United States Patent
McPherson et al.

(10) Patent No.: US 7,131,605 B2
(45) Date of Patent: Nov. 7, 2006

(54) AUTOMATIC BONE MILL

(75) Inventors: Cameron McPherson, Fort Worth, TX (US); Sreenivas Chowdiah, Plano, TX (US); Scott A. Singer, Fort Worth, TX (US); Rob Ellins, Euless, TX (US); Kevin Foley, Germantown, TN (US)

(73) Assignee: Medtronic, Inc., Minneapolis, MN (US)

( * ) Notice: Subject to any disclaimer, the term of this patent is extended or adjusted under 35 U.S.C. 154(b) by 161 days.

(21) Appl. No.: 10/749,316

(22) Filed: Dec. 31, 2003

(65) Prior Publication Data

US 2004/0155132 A1 Aug. 12, 2004

Related U.S. Application Data

(63) Continuation-in-part of application No. 10/184,444, filed on Jun. 28, 2002, now Pat. No. 6,824,087.

(51) Int. Cl.
*B02C 19/00* (2006.01)

(52) U.S. Cl. ............... 241/199.12; 241/282.1; 241/285.2

(58) Field of Classification Search ............... 241/100, 241/282.1, 282.2, 285.1, 285.2, 199.12
See application file for complete search history.

(56) References Cited

U.S. PATENT DOCUMENTS

| 4,101,082 A | 7/1978 | Mayer et al. |
| 4,469,283 A | 9/1984 | Noguchi et al. |
| 5,810,472 A | 9/1998 | Penaranda et al. |

OTHER PUBLICATIONS

IKA A11 Basic, www.ika.de/ika/English/features/allbasic.html.
M20 IKA Universal Mill—www.ika.de/ika/English/home.html.

*Primary Examiner*—Mark Rosenbaum
(74) *Attorney, Agent, or Firm*—Haynes and Boone, LLP

(57) ABSTRACT

A bone mill for use in a surgical or otherwise sterile environment includes a particle reducer such as a pulverizing blade, a motor such as an electrical motor, and a coupling such as a rotary shaft for connecting the particle reducer to the motor.

20 Claims, 11 Drawing Sheets

AUTOMATIC BONE MILL

CROSS-REFERENCE TO RELATED APPLICATIONS

This is a continuation-in-part of patent application Ser. No. 10/184,444, filed on Jun. 28, 2002, Automatic Bone Mill, now U.S. Pat. No. 6,824,087, assigned to same assignee as the present invention, which is incorporated by reference in its entirety.

FIELD OF THE INVENTION

The present invention generally relates to surgical instruments and their use. More particularly, the present invention relates to a bone mill for use in a surgical, medical, or other environment where ground bone particles are needed.

Ground bone particles can be used in various medical and surgical procedures. For example, finely ground bone particles can be used for spinal fusions, to repair defects caused by trauma, transplant surgery, or tissue banking. In this example, a surgeon may remove a portion of bone from a patient, grind the portion into fairly homogenous particles using a hand-powered rasp, and use the bone particles to patch and repair another area of bone, such as on the patient's spinal cord or skull. The step of grinding the portion of bone using a hand-powered rasp is a relatively long and strenuous operation, with mixed results depending on the bone, the rasp, and the operator's ability.

As with all instruments used in surgery, the hand-powered rasp must be sterile, and must maintain a sterile environment during a surgical procedure. Typically, a surgical instrument is sterilized before and/or after the surgical procedure to disinfect the instrument and remove any toxic debris and other contaminants. Instruments such as the hand-powered rasp are typically disassembled, sterilized using an autoclave or other sterilization procedure, and then reassembled. This process also introduces an element of time and expense that must be accounted for in the surgical procedure.

Furthermore, rasps in general have certain deficiencies. Rasps are inherently wasteful, it being difficult to remove all of the bone particles there from. Also, there is no way to mix various additives to the bone particles, such as an additive that promotes bone growth, during the milling process.

SUMMARY OF THE INVENTION

It is an object of the present invention to overcome the above disadvantages of the conventional hand-powered rasp to provide a system and method that can be used to break up bone and/or other material in a sterile environment.

In one embodiment, the present invention provides an automatic surgical mill for use in a sterile environment. The mill includes a particle reducer positioned inside a sterile compartment, a motor for providing a rotational force, and a coupling for connecting the particle reducer to the motor. When the rotational force is provided, the coupling translates the force to the particle reducer.

In some embodiments, the coupling includes a first coupling member for selectively connecting and disconnecting the particle reducer to the motor.

In some embodiments, the mill includes a first casing for housing the particle reducer and forming the sterile compartment. In this way, the first casing and particle reducer can be separated from the motor and can be separately sterilized or disposed of following use.

In some embodiments, the first casing comprises means for receiving a cover, so that the cover can be selectively positioned to cover at least a portion of the coupling when the first casing is separated from the motor.

In another embodiment, an automatic bone mill includes a cup-like mill casing body defining a cutter receiving space. The mill casing body includes an open upper end for detachably connecting with a mill casing cover. A rotatable pulverizing cutter is positioned in the cutter receiving space and a torque transfer device for providing a rotational force to the rotatable pulverizing cutter is provided. The torque transfer device is adaptable to connect to a motor for providing the rotational force. The mill casing body, the mill casing cover, and the rotatable pulverizing cutter are capable of maintaining a sterile environment by being separated from the motor.

In some embodiments, the bone mill also includes a cover connectable to the mill casing body for covering a portion of the torque transfer device when the torque transfer device is not connected to the motor.

In some embodiments, the cover is rotatable to uncover the portion of the torque transfer device so that the torque transfer device can connect to the motor.

In some embodiments, the torque transfer device includes a multifaceted shaft for connecting with a multifaceted receiving member.

In some embodiments, the bone mill device also includes a switch attached to the cup-like mill casing body. The switch can be used for controlling an operation of the motor when the torque transfer device is connected to the motor. In some embodiments, the switch controls the operation of the motor through an electrical signal, and the electrical signal may pass from the switch to the motor through the torque transfer device. In other embodiments, the electrical signal can pass from the switch to the motor through the cup-like mill casing body.

In some embodiments, the mill casing cover includes an opening for receiving the bone or other material into the cutter receiving space. The opening can also be used to connect to a device, such as a syringe, for receiving the bone or other material after the bone or other material has been milled.

In another embodiment, a bone cutting device for use in a surgical environment includes a pulverizing blade and a rotatable shaft connected to the blade. The rotatable shaft is selectively connectable to a powered surgical instrument, such as a powered bone dissecting instrument.

In some embodiments, the bone cutting device includes a casing for surrounding the pulverizing blade and means, such as a slidable sleeve, for selectively attaching the casing to the powered surgical instrument.

In some embodiments, the rotatable shaft fits on a collet of the powered surgical instrument.

In another embodiment, a hand-held powered bone mill for use in a sterile environment includes a casing for surrounding and securing a motor and for defining a chamber for receiving bone and other material. The casing is shaped to be easily held by a single hand of a user. The hand-held powered bone mill also includes a rotatable shaft connected to the motor and extending into the chamber, and a particle reducing device connected to the rotatable shaft for impacting the bone and other material in the chamber. A switch can be connected to the casing and activatable by the user when the user is holding the casing, the switch for selectively controlling an operational mode of the motor.

In another embodiment, an automatic bone mill for use in a surgical environment includes first and second casing portions for defining a milling chamber and for selectively attaching and de-attaching with each other. The automatic bone mill also includes a particle reducer including a blade disposed in the milling chamber and a first shaft extending from the blade through the second casing portion. A motor provides a rotational force to a second shaft and is surrounded by a third casing portion, which also selectively attaches and de-attaches with the second casing portion. A detachable coupling is also provided for selectively engaging the first shaft with the second shaft.

In some embodiments, the detachable coupling engages the first and second shafts whenever the second and third casing portions are attached.

In some embodiments, the detachable coupling includes a first member attached to the first shaft, and the second casing portion includes a recessed area for housing the first shaft and a cover for selectively covering the first shaft in the recessed area.

In another embodiment, a method of using a bone mill in a sterile environment is provided. The method includes placing a piece of bone inside a sterile casing, the sterile casing including a sterile bone particle reducer connected to a sterile shaft extending externally from the casing. The sterile shaft is connected to a motor and the motor is activated to rotate the sterile bone particle reducer, thereby milling the bone.

In some embodiments, the motor may not be sterile, and may be covered with a sterile cover such as a sheet or bucket.

In some embodiments, the shaft is covered with a sterile cover after removing it from the motor. The shaft can be removed from the motor and the milled bone from the sterile casing.

In some embodiments, the motor, casings, and other components can be autoclaved and placed in a sterile environment. In other embodiments, one or more of the components can simply be covered with a sterile cover in a non-sterile environment. In either way, the casing that forms the milling container can be attached and removed from the motor without compromising the sterility of the container or its contents.

In another embodiment, an automatic surgical mill is provided, which includes a unitary casing, the unitary casing having an opening through which bone is introduced into the mill, a rotatable pulverizing cutter positioned inside a first compartment of the casing, a motor for providing a rotational force, the motor being positioned within a second compartment of the casing, and a coupling for connecting the cutter to the motor so that the rotational force provided by the motor is imparted to the particle reducer, thereby pulverizing bone introduced into the mill.

In another embodiment, an automatic surgical mill for pulverizing bone is provides, which includes a first casing member for housing a rotatable pulverizing cutter, the first casing member having an opening for receiving bone into the first casing member, a second casing member selectively connectable with the first casing member, the second casing member housing a coupling, a first sealing arrangement disposed between the first and second casing members, a third casing member selectively connectable with the second casing member, the third casing member housing a motor, and a second sealing arrangement disposed between the second and third casing members.

In yet another embodiment, a bone mill assembly is provided, which includes an automatic surgical mill having means for receiving and housing bone in a casing, means for pulverizing bone housed within the casing, and means for removing the pulverized bone from the housing.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Various other objects, features and attendant advantages of the present invention will be more fully appreciated as the same becomes better understood from the following detailed description when considered in connection with the accompanying drawings, and wherein.

DETAILED DESCRIPTION

Figure 1:
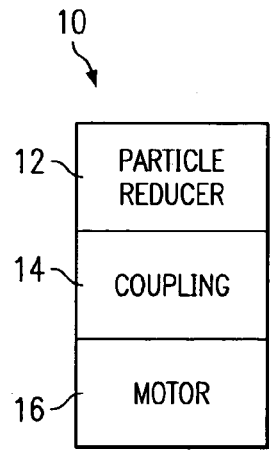
FIG. 1 is a block diagram of an automatic bone mill for implementing features of the present invention.

The following description of the preferred embodiments is merely exemplary in nature and is in no way intended to limit the invention, its application, or uses. In addition, the following description may repeat reference numerals and/or letters in the various embodiments. This repetition is for the purpose of simplicity and clarity and does not in itself dictate a relationship between the various embodiments and/or configurations discussed.

Referring to FIG. 1, the reference numeral 10 designates, in general, an automatic bone mill for implementing features of the present invention. The bone mill 10 includes a particle reducer 12, a coupling 14, and a motor 16. The particle reducer 12 is capable of reducing one or more pieces of bone and/or other material into smaller particles. The motor 16 is used for moving the particle reducer in an automatic fashion. The coupling 14 is for connecting the motor 16 to the particle reducer 12, and in some embodiments, may allow for relatively easy connection and disconnection of the particle reducer to and from the motor.

Figure 2:
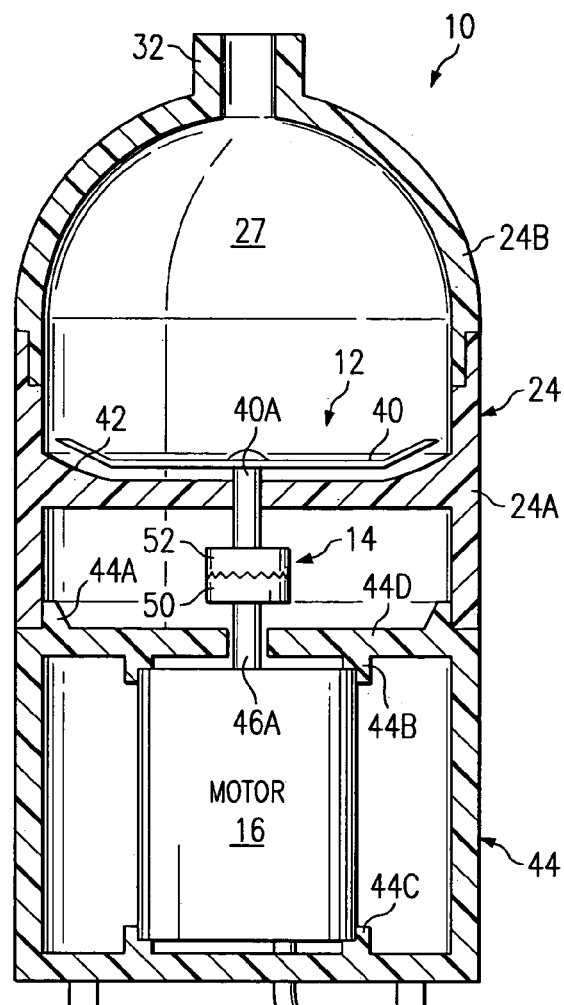
FIG. 2 is a sectional view of a first embodiment of the bone mill of the present invention.
Figure 3:
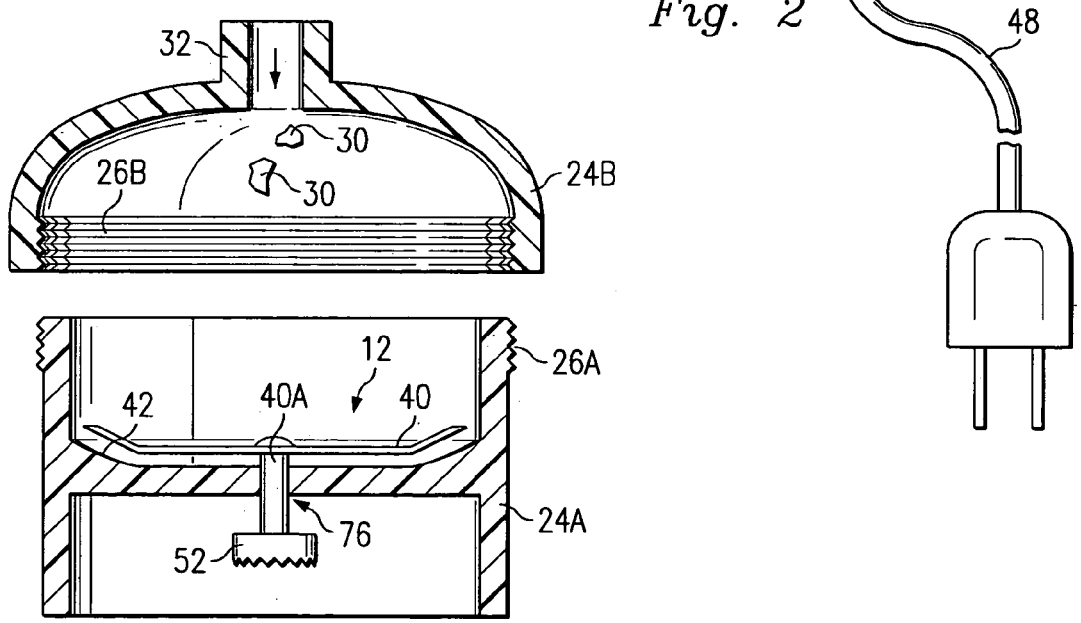
FIG. 3 is a sectional view of a compartment casing body and cover of the bone mill of FIG. 2.
Figure 4A:
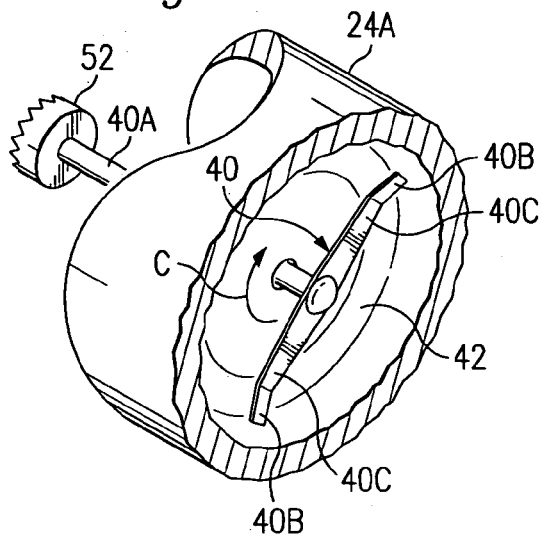
FIG. 4A is a perspective view of the compartment casing body of FIG. 3 and a particle reducer.
Figure 4B:
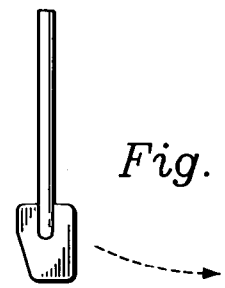
FIG. 4B is a sectional view of the compartment casing cover of FIG. 3 being used in a novel manner.
Figure 4B:
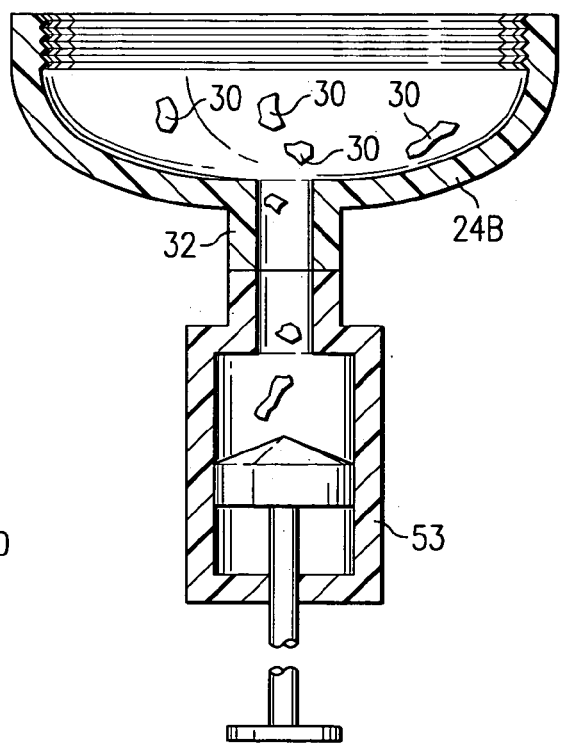

Referring to FIGS. 2–4, in one embodiment, the particle reducer 12 is positioned inside a compartment casing 24. The compartment casing 24 includes a cylindrical cup-like compartment casing body 24A whose top is open and a cylindrical cup-like compartment casing cover 24B made of a semitransparent synthetic resin, which is detachable. In one embodiment (shown in FIG. 2), the compartment casing body 24A and cover 24B frictionally engage for selectively securing the two. Although not shown, one or more recess/protrusions points can be included in the compartment casing body 24A and cover 24B so that when the two are being engaged, they "snap" together and are held by the combination of the recess and protrusion. In another embodiment (shown in FIG. 3), the compartment casing body 24A and cover 24B include opposing sets of screw threads 26A, 26B, respectively, for selectively securing and separating the two. It is understood that there are many different mechanisms for selectively securing and separating the compartment casing body 24A and cover 24B. When secured, the compartment casing body 24A and cover 24B form a chamber 27 for receiving bone, blood, or other material 30.

In some embodiments, the bone mill 10 is adapted to protect against operation of the particle reducer 12 prior to placement of the cover 24B on the compartment casing body 24A. For example, referring to FIG. 14, the compartment casing body 24A may include an indicia 140, or otherwise engageable element, for communicating with the motor 16 to indicate readiness for use. Upon engagement of the cover 24B with the indicia 140, a switch (not depicted) is activated, which closes a motor circuit associated with the motor 16, thereby rendering the motor, and therefore, the particle reducer 12 operable. Accordingly, during instances in which the indicia 140 is not engaged by the cover 24B, the switch is deactivated, which opens the motor circuit, thereby rendering the motor 16 inoperable, and ensuring inoperability of the particle reducer 12.

Referring again to FIGS. 2–4, in the present embodiment, the compartment casing cover 24B includes an opening 32. The opening 32 can be used for inserting the material 30, and can be used as a view port by a user. The opening can also be used for additional purposes discussed in further detail below. It is understood that some embodiments may not have any opening, while other embodiments may have several openings. For embodiments with openings, it may be desirable to temporarily close or cover the opening during one or more operations.

In some embodiments, the particle reducer 12 uses a blade 40 for converting the material 30 into smaller pieces. In the present embodiment, the blade 40 is a bone pulverizing metallic cutter including a rotary shaft 40A. By pulverizing the bone 30, the blade 40 can remain relatively dull, breaking the bone by impact instead (or in addition to) cutting the bone. The illustrated blade 40 includes two flat blade portions 40C, each fixed to and extending radially and horizontally from the rotary shaft 40A, and two radially outwardly raised portions 40B fixed to the radially outer end of the horizontal portions 40C. In addition to an improved pulverizing design, the combinations of the flat blade portions 40C and the raised portions 40B allow the blade 40 to substantially follow the curvature of a bottom surface 42 of the cup-like compartment casing body 24A, thereby engaging with most of the material 30 that may be in the chamber 27. It is understood that other embodiments may have one or more different or additional particle reducing apparatuses, such as a relatively sharp blade.

Figure 15:
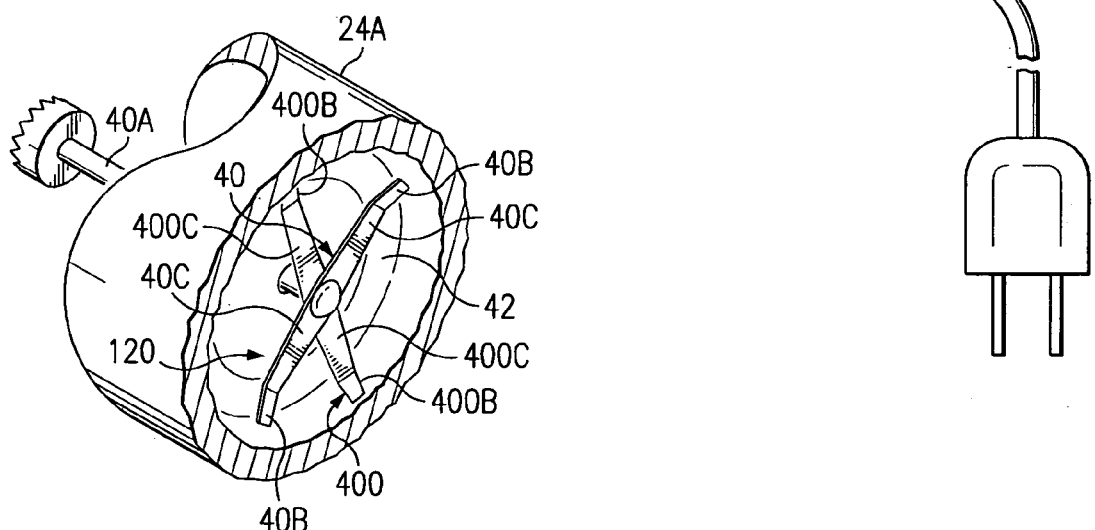
FIG. 15 is a perspective view of a portion of an alternative bone mill and a particle reducer associated with the bone mill.

For example, and referring to FIG. 15, an alternative particle reducer 120 may include a sharp blade 400 in addition to the blade 40 such that the distal ends of the blade 40 are interposed with the distal ends of the blade 400. In one embodiment, the blade 400 is similar to blade 40 in having two flat blade portions 400C, each fixed to and extending radially and horizontally from the rotary shaft 40A, and two radially outwardly raised portions 400B fixed to the radially outer end of the horizontal portions 400C. Accordingly, like the blade 40, blade 400 is constructed to follow the curvature of the bottom surface 42 of the cup-like compartment casing body 24A, thereby engaging with most of the material 30 that may be in the chamber 27. As can be appreciated, any number of blades 40 and 400, or other alternative blades, may be provided with the particle reducer 12, and the degree of sharpness associated with such blades can vary to meet desired operating conditions.

Figure 16:
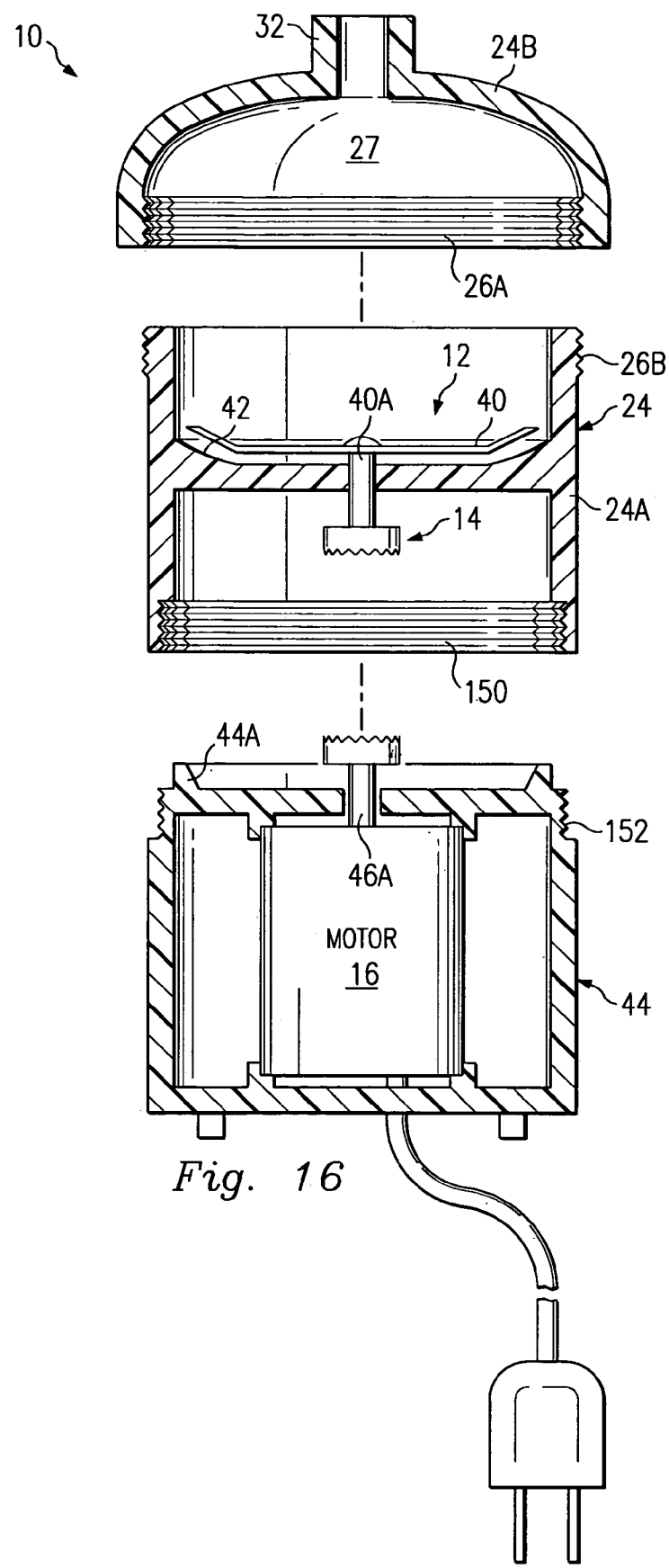
FIG. 16 is an exploded, sectional view of an alternate embodiment of the bone mill of the present invention.

Referring again to FIGS. 2–4, in the present embodiment, the compartment casing 24 is detachably mounted to a hollow motor casing 44. The motor casing 44 is made of a synthetic resin which holds the motor 16, although other materials may also be used. When the compartment casing 24 is mounted on the motor casing 44, the inner periphery of the lower end of the compartment casing body 24A is frictionally fitted to a rib 44A of the motor casing 44 to prevent easy detachment. The rib 44A is formed in the surface of the upper wall of the hollow motor casing to fit with the lower end of a compartment casing 24 which is described below. It is understood that some embodiments may not engage the compartment casing 24 with the motor casing 44 at all, while other embodiments may use different or additional mechanisms, such as those discussed above for securing the compartment casing body 24A and cover 24B. For example, referring to FIG. 16, the compartment casing 24 and the motor casing 44 may alternatively include opposing sets of screw threads 150, 152, respectively, for selectively securing and separating the two.

Referring again to FIGS. 2–4, the motor casing 44 also includes motor supporters 44B and 44C for securing the motor 16. A rotor shaft 46A of the motor extends from an upper wall 44D of the motor casing 44 and is driven in the direction C (FIG. 4A) by enabling the motor through a power source such as an electrical outlet or battery, represented generically by a power cord 48 shown in phantom.

As shown in FIG. 3, the compartment casing body 24A can be separated from the motor casing 44. In this way, the compartment casing 24 can be easily moved from one place to another. For example, in a surgery room, the motor 16 can be located away from the sterile field—which is a defined area that must maintain in a sterile environment. A person in the operating room can place the material 30 in a sterile compartment formed by the casing 24, take the material 30 and casing 24 to the motor 16 to mill the material, and return the milled material to the sterile field without compromising the sterility of the compartment or the processed material. The compartment casing 24 and/or the particle reducer 12 can also be disposable.

To facilitate the separation of the compartment casing 24 to and from the motor casing 44, the coupling 14 includes a first coupling member 50 and a second coupling member 52. The first coupling member 50 is secured to the motor's rotor shaft 46A, and the second coupling member 52 is secured to the rotary shaft 40A. As shown in FIG. 2, the first and second coupling members 50, 52 have interlocking "teeth" that can be used to transfer rotational movement in the direction C, but allow for the vertical (as shown in FIG. 2) separation of the two.

Figure 17:
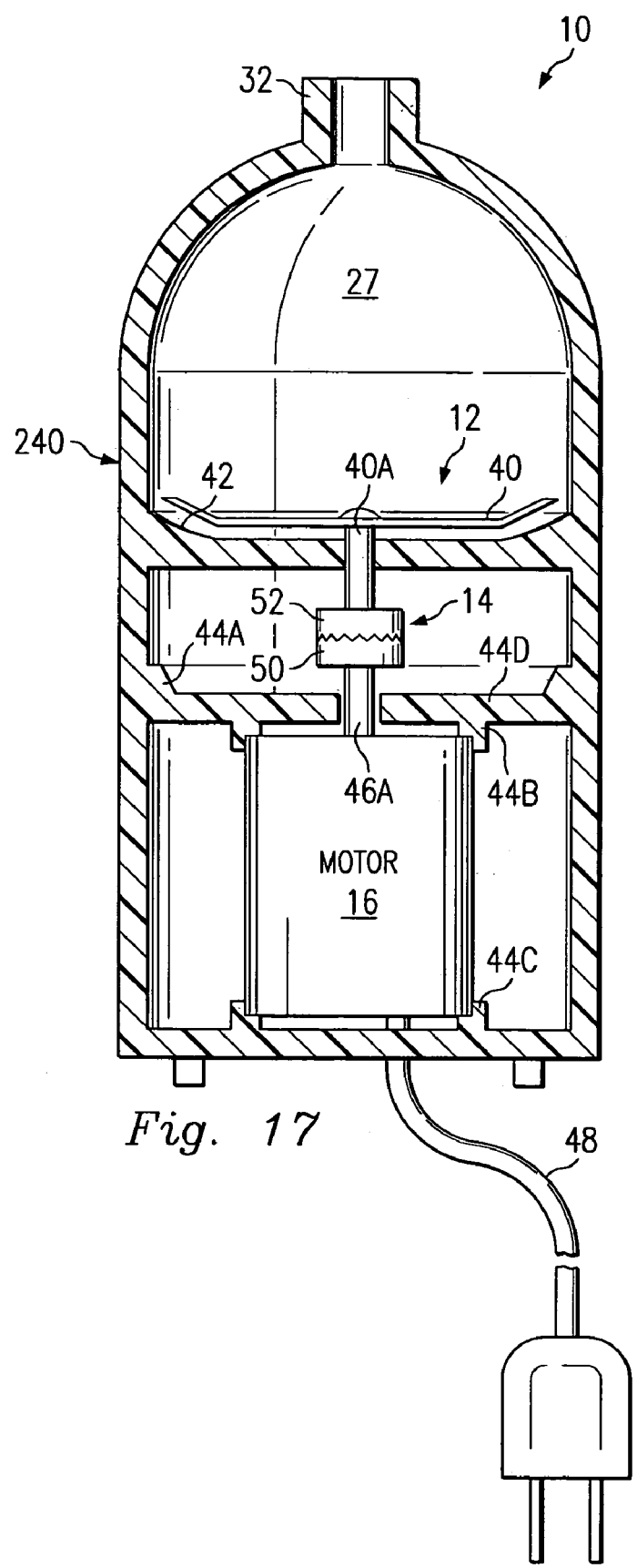
FIG. 17 is a sectional view of an alternate embodiment of the bone mill of the present invention.

Referring to FIG. 17, in other embodiments, the bone mill 10 may be formed unitarily such that the compartment casing body 24A, the cover 24B, and the motor casing 44 are replaced with a single-piece casing 240. A unitary bone mill 10 could be configured as a sterilizable, reusable device, or a non-sterilizable, single-use device. Moreover, a unitary bone mill 10 further guards against dangers associated with improper operation of the particle reducer 12.

Figure 5A:
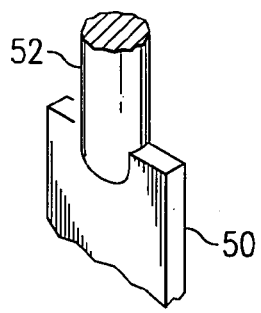
FIGS. 5A and 5B are alternate embodiments of a coupling, such as can be used with the bone mill of FIG. 2.
Figure 5B:
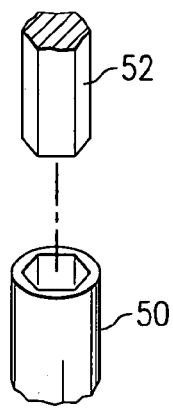

Referring to FIGS. 5A and 5B, different embodiments of the coupling 14 may include different shaped coupling members 50, 52. With the embodiments shown in FIGS. 5A and 5B, the blade 40 and shaft 40A can be easily removed and inserted through an opening 76 (FIG. 3) of the compartment casing body 24A.

Referring to FIGS. 2–4, a process for pulverizing material in the bone mill 10 will now be described. Bone and/or other material 30 is put into the chamber 27 formed in the compartment casing body 24A. This can be done after taking off the bone mill cover 24B or by dropping the material 30 through the opening 32. The compartment casing cover 24B is placed onto the compartment casing body 24A, which is further placed onto the motor casing 44 as shown in FIG. 1 (if either were previously removed). A switch can then be activated to turn on the motor 16, whereby the motor is rotated at high speed in the direction shown by the arrow C in FIG. 4A. The rotational force of the motor is transmitted through the first coupling member 50 and the second coupling member 52 to the blade 40. The bone 30 is pulverized by the blade 40 rotating at high speed.

Referring to FIG. 4B, in some embodiments, once the material 30 has been pulverized (or otherwise reduced in size), the compartment casing 24 can be separated from the motor 16 and moved to a different location (such as the sterile field if the motor 16 is not already there). The compartment casing cover 24B can then be separated from the compartment casing body 24A and used as a bowl for mixing and or stirring the pulverized material 30. A tool, such as a spatula S, can be used to help move some of the material 30 away from the blade 40 and the compartment casing body 24A and into the cover 24B. In the embodiments that include the opening 32, a syringe 53 or other receptacle can be connected to the opening 32 of the compartment casing cover 24B to receive the pulverized material 30 for later use.

Figure 6:
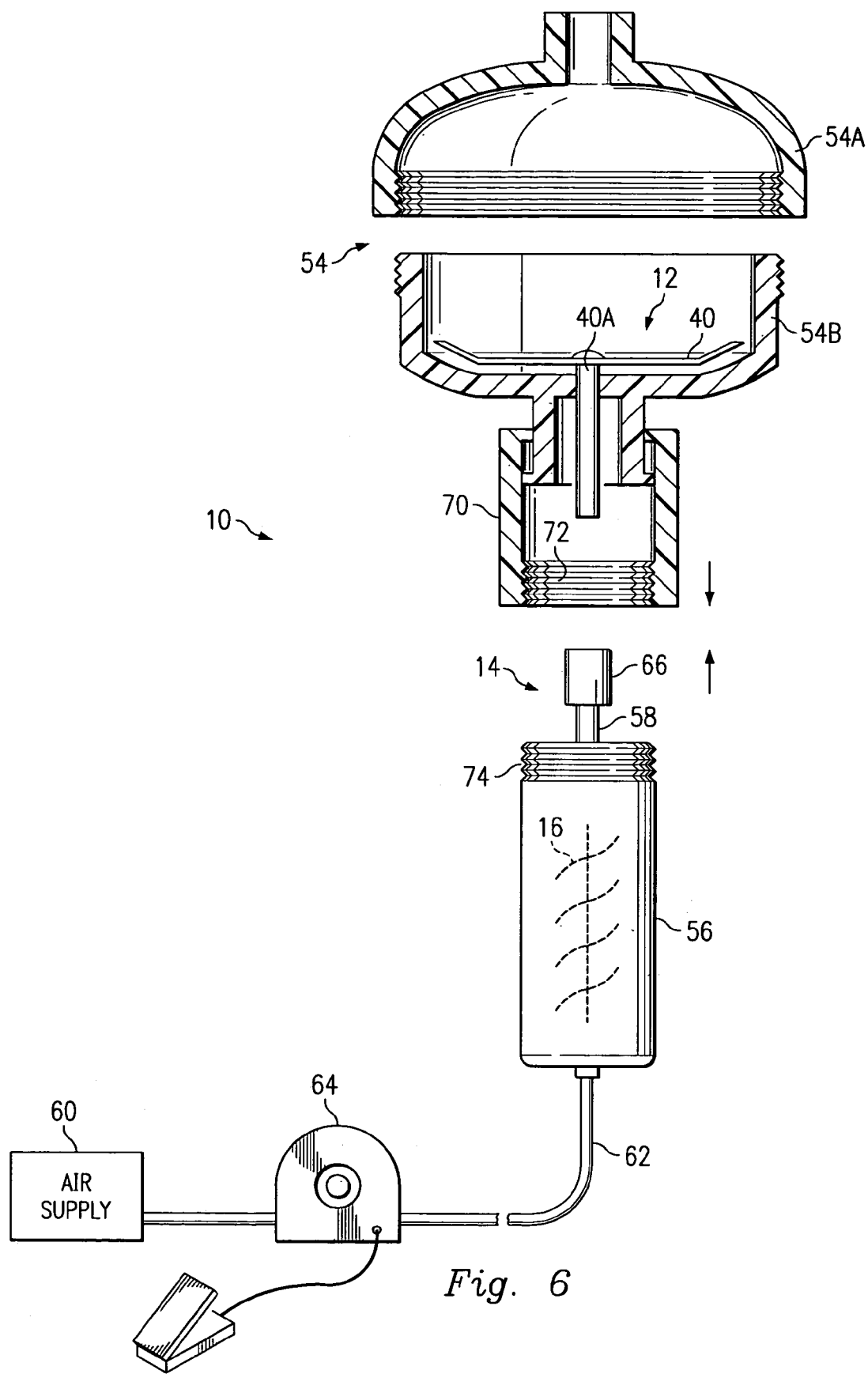
FIG. 6 is a side view of another embodiment of the bone mill of the present invention.

Referring to FIG. 6, in another embodiment, the particle reducer 12 is positioned inside a compartment casing 54. The compartment casing 54 includes a cylindrical cup-like compartment casing body 54A whose top is open and a cylindrical cup-like compartment casing cover 54B made of a semitransparent synthetic resin, which is detachable. In many ways, the compartment casing 54 is similar to the compartment casing 24 of FIG. 2, with one difference being the manner in which the compartment casing connects to the motor 16.

In the present embodiments, the motor 16 is part of an existing powered instrument 56 commonly used in surgery, such as the MIDAS CLASSIC brand pneumatically powered bone dissecting instrument manufactured by Medtronic Midas Rex of Fort Worth, Tex. It is understood that the MIDAS CLASSIC brand instrument is merely an example, and other powered surgical instruments, including electrically powered instruments and/or those from other manufacturers, can be used.

In the present embodiment, the surgical instrument 56 includes the pneumatic motor 16 powered by a regulated air supply 60 connected through an air hose 62. The air supply is further controlled through a foot switch 64 for selectively activating the pneumatic motor 16. The surgical instrument 56 also includes a rotor shaft 58 connected to a collet 66. The collet 66 serves as the first coupling member 50 of the coupling 14. However, in this embodiment, the collet 66 attaches directly to the rotary shaft 40A of the blade 40 and provides rotational force to the rotary shaft.

It is understood that there are many different types of collets, some requiring a corresponding second coupling member 52, others not, that can be used. For example, referring also to FIG. 6B, a multi-faceted version of the second coupling member 52, which is a shaped portion of the rotor shaft 40A, can be inserted into the first coupling member 50, which is a corresponding quick-release collet assembly. This example of collet assembly is used in the MIDAS LEGEND brand surgical instrument, disclosed in U.S. Ser. No. 10/102,762, which is hereby incorporated by reference.

In some embodiments, the compartment casing 54 is not attached to the surgical instrument 56. In other embodiments, such as is shown in FIG. 6, the compartment casing 54 can be mounted onto the surgical instrument 56. For use with the MIDAS CLASSIC brand surgical instrument, the compartment casing 54 includes a slidable sleeve 70 with internal threads 72 for selectively engaging with opposing threads 74 on the surgical instrument 56. The slidable sleeve 70 further allows access to the coupling 66 for connecting and removing the particle reducer 12.

Figure 7:
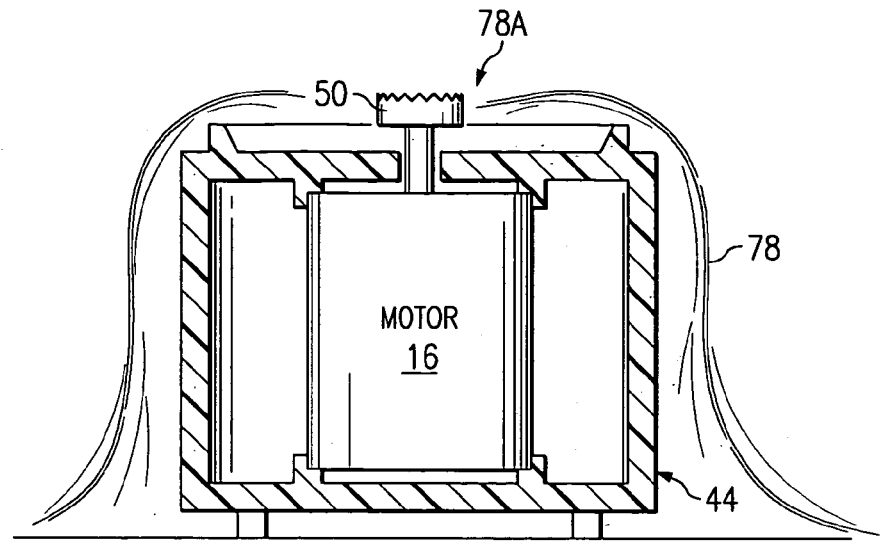
FIG. 7 is a cross sectional view of a motor covered by a sterile sheet, such as can be used with the bone mill of FIG. 2.

Referring to FIG. 7, the motor 16 can also maintain a sterile environment by using a sterile sheet or "bucket," designated generally by the reference numeral 78. In the present embodiment, the sterile sheet/bucket 78 includes an opening 78A through which the first coupling member 50 extends. In other embodiments, the sterile bucket 78 may include a rotatable cover that can be situated between the two couplings 50, 52 and transfer the rotational force from the first coupling member to the second. By using a sterile sheet or sterile bucket 78, or some other type of sterile cover, the motor 16 does not have to be sterilized, and does not have to go through any autoclave cycle. However, in other embodiments, the motor 16 and motor casing 44 are sterilizable, thus eliminating the need for the sterile sheet 78. For example, the motor 16 and motor casing 44 could take the form of one-time sterilizable, e.g. gamma irradiated, single-use device, or a sterilizable reusable device.

Figure 8:
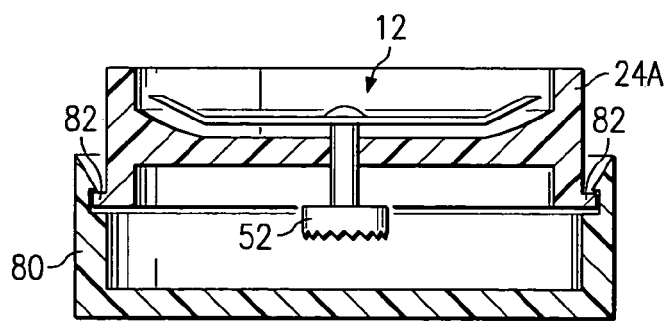
FIGS. 8 and 9A are cross sectional view of different embodiments of the compartment casing bodies, such as can be used with the bone mill of FIG. 2.
Figure 9A:
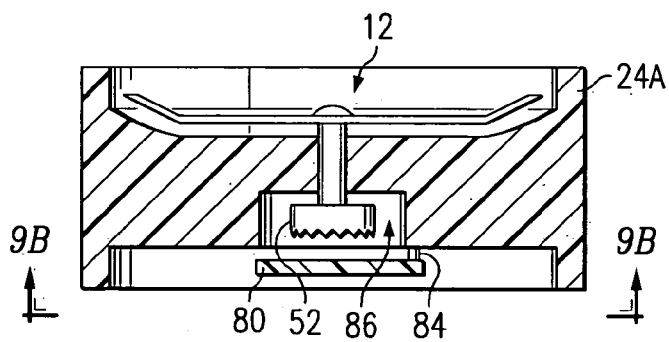
Figure 9B:
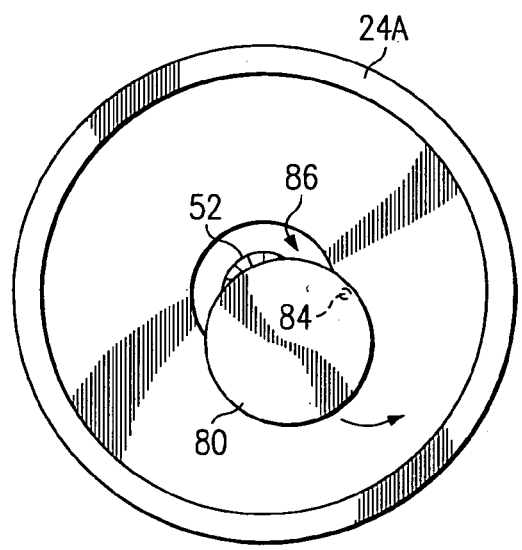
FIG. 9B is a perspective view of FIG. 9A.

Referring to FIGS. 8, 9A, and 9B, in some embodiments, a cover 80 can be used to cover or seal the second coupling member 52. In the embodiment of FIG. 8, the cover 80 can snap onto a lip 82 of the compartment casing body 24A and be removed as required. In the embodiment of FIGS. 9A and 9B, the cover 80 is rotationally attached to the compartment casing body 24A at a pivot point 84. This allows the cover 80 to rotate into a first position to seal the second coupling member 52, which is in a recessed area 86 of the compartment casing body 24A, and to rotate to a second position, away from the second coupling member, to allow the second coupling member to engage with the first coupling member 50.

The cover 80 provides an extra level of sterile protection. For example, sometimes when using the motor 16 and the sterile sheet/bucket 78 of FIG. 7, the coupling 14 will not remain sterile. As a result, the second coupling member 52 becomes contaminated. By using the cover 80, however, the second coupling member 52 becomes enclosed, and therefore cannot further contaminate anything else in the sterile environment. Also, the coupling member 52 can be sterile, detachable, and disposable, so that it can be removed after operation.

Another important factor in maintaining a sterile environment is how the motor 16 is controlled (e.g., turned on and off). For example, if the motor 16 is covered by the sterile sheet/bucket 78, it may be difficult to access a switch at a conventional location on the motor.

Referring again to FIG. 6, in one embodiment, the foot switch 64 is used to selectively enable an air supply to the pneumatic motor 16. A similar foot switch can also be used to selectively enable an electric supply to an electric motor as well. A benefit of using the foot switch 64 is that the switch is placed on or near the floor, which is located out of the sterile field.

Figure 10:
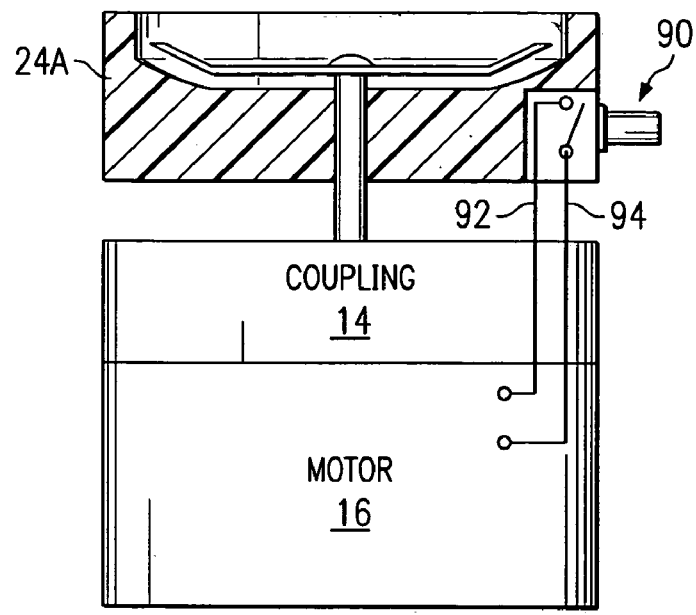
FIGS. 10 and 11 are cross sectional view of different embodiments of switches, such as can be used with the bone mill of FIG. 2.

Referring to FIG. 10, in another embodiment, a switch 90 is positioned on the compartment casing body 24A. In the present example, the switch 90 is an electric switch. The switch 90 is in electrical contact with the motor 16 through connectors 90, 92. Although the illustration of FIG. 9 shows the two connectors 92, 94 as wires, other embodiments are also anticipated. For example, referring also to FIG. 2, the couplings 50, 52 may include an electrically conductive material so that they also serve as one (or both) of the connectors 92, 94. Also, the compartment casing body 24A and the motor casing 44 may include an electrically conductive portion that serves as one (or both) of the connectors 92, 94 when the two are joined (as illustrated in FIG. 2). These embodiments have the extra advantage of preventing operation of the mill 10 when the particle reducer 12 is not properly attached to the motor 16.

Figure 11:
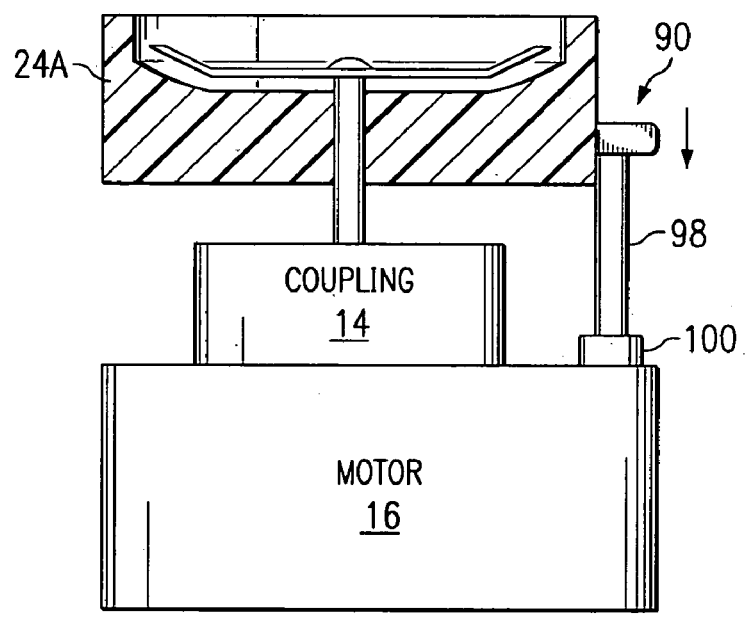

Referring to FIG. 11, in another embodiment, a mechanical actuator 96 is positioned on the compartment casing body 24A. The mechanical actuator 96 is further attached to an extender 98 that is positioned next to a switch 100 for controlling the motor 16. An advantage of this embodiment is that it works well when the motor 16 is covered by the sterile sheet/bucket 78 (FIG. 7). For example, the extender 98 may project through the opening 78A in the sterile sheet/bucket 78.

Figure 12:
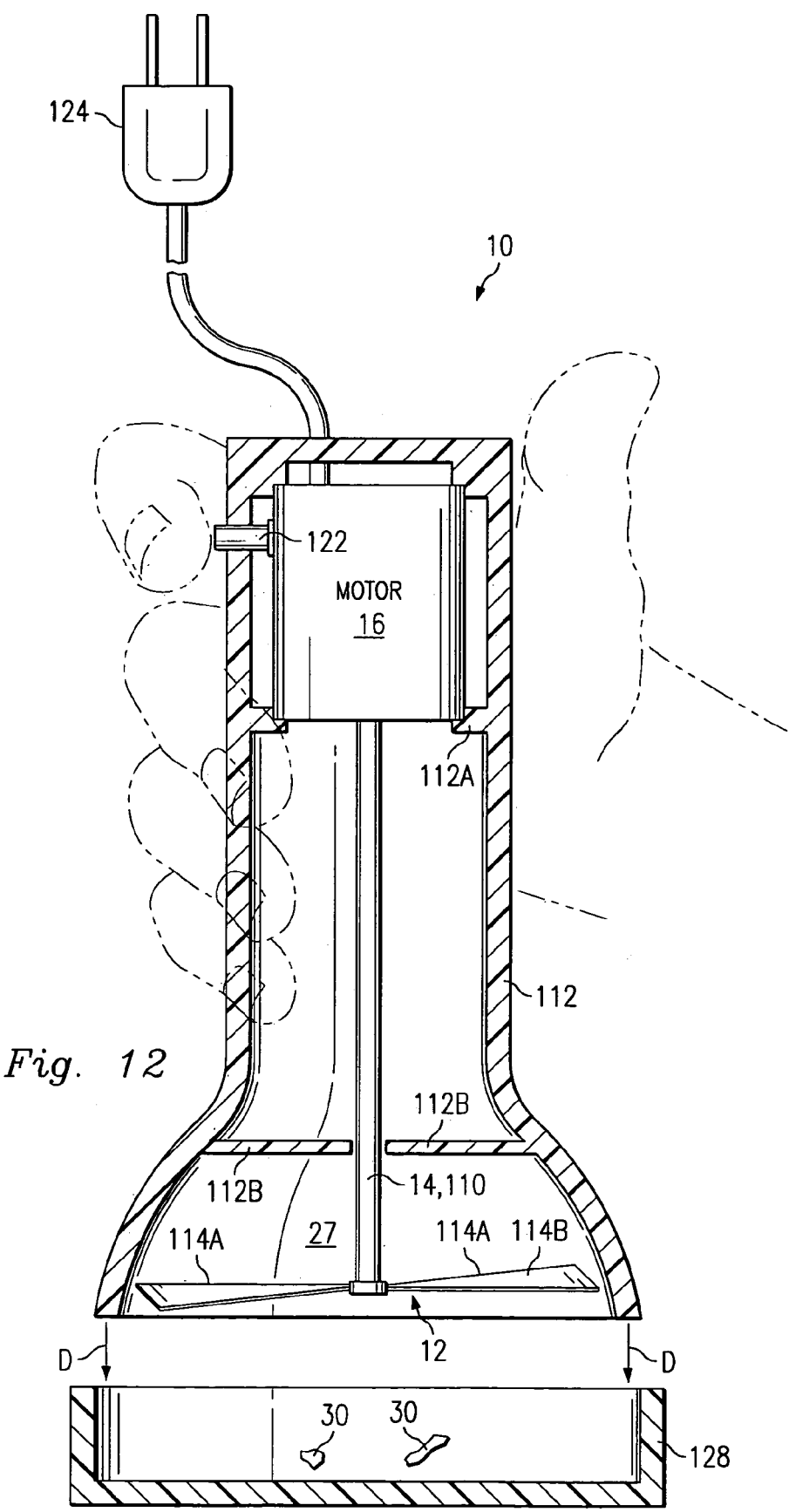
FIGS. 12 and 13 are cross sectional views of other additional embodiments of the bone mill of the present invention.

Referring now to FIG. 12, it is understood that some embodiments of the coupling 14 may not be readily detachable. For example, the motor 16 can be permanently attached to the particle reducer 12 by a straight shaft 110. In the present embodiment of FIG. 12, a monolithic casing 112 houses the motor 16 with motor supports 112A, and surrounds the particle reducer 12. Also, the particle reducer 12 includes a relatively sharp edge 114a and a fin 114b for moving air and/or the material 30 inside the chamber 27. The casing 112 also includes a wall portion 112B for further defining the chamber 27 and keeping any material 30 from getting near the motor 16. The entire system 10 can be either autoclavable or disposable.

In operation, the monolithic casing 112 is moved towards a container 120, as illustrated by arrows D, to further seal the chamber 27. In the present embodiment, a user may then activate a switch 122 which selectively connects the motor 16 to an external power source represented by the power cord 124. It is understood that in some embodiments, the power cord 124 is of the type that is autoclave-able. When activated, the motor 16 rotates the particle reducer 12 through the straight shaft 110, thereby causing the sharp edge 114a to cut the material 30 that is located in a container 128.

Figure 13:
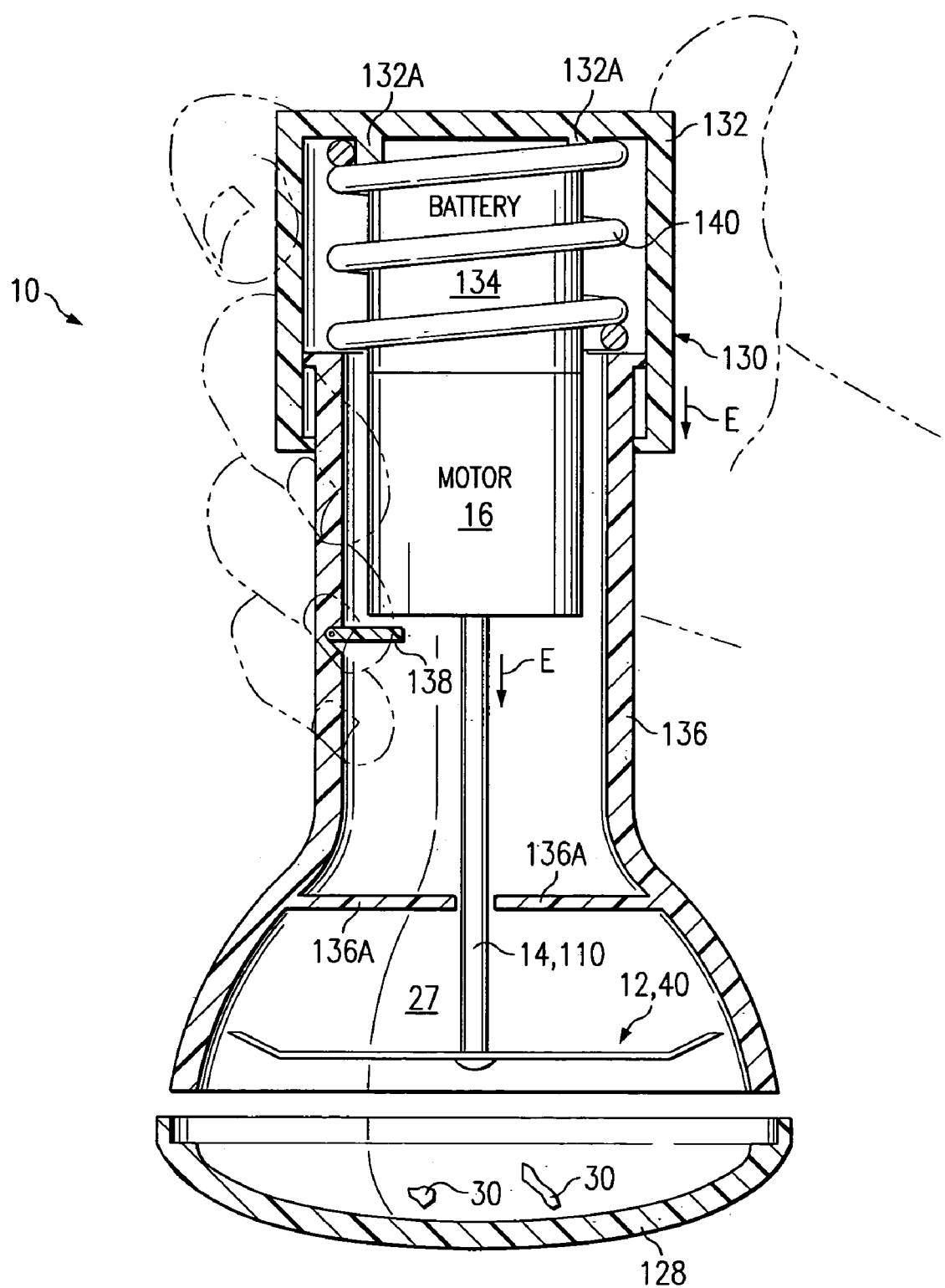

Referring to FIG. 13, in still another embodiment, a two-piece casing 130 surrounds and protects the motor 16, the coupling 14, and at least a portion of the particle reducer 12. In the present embodiment, the coupling 14 includes the straight shaft 110 shown in FIG. 12 and the blade 40 shown in FIG. 4A.

One piece of the casing 130 is a handle body 132, which serves as a gripping area so that the mill 10 can be hand-held by a user. In the present embodiment, the handle body 132 includes motor supports 132A connected to the motor 16. Also in the present embodiment, the motor 16 includes a battery 134, but it is understood that other embodiments may be powered with other conventional methods. The other piece of the casing 130 is a main body 136 for surrounding the straight shaft 110 and at times, the blade 40. The main body 136 includes a wall portion 136A for further defining the chamber 27 and keeping any material 30 from getting near the motor 16. A switch 138 is attached to the main body 136 and the motor 16 for selectively enabling the motor as discussed in further detail below.

A spring 140 is imposed within the handle body 132 and the main body 136. The spring 140 encourages the handle body 132 to separate from the main body 136, opposite to the direction of arrow E illustrated in the figure.

Figure 14:
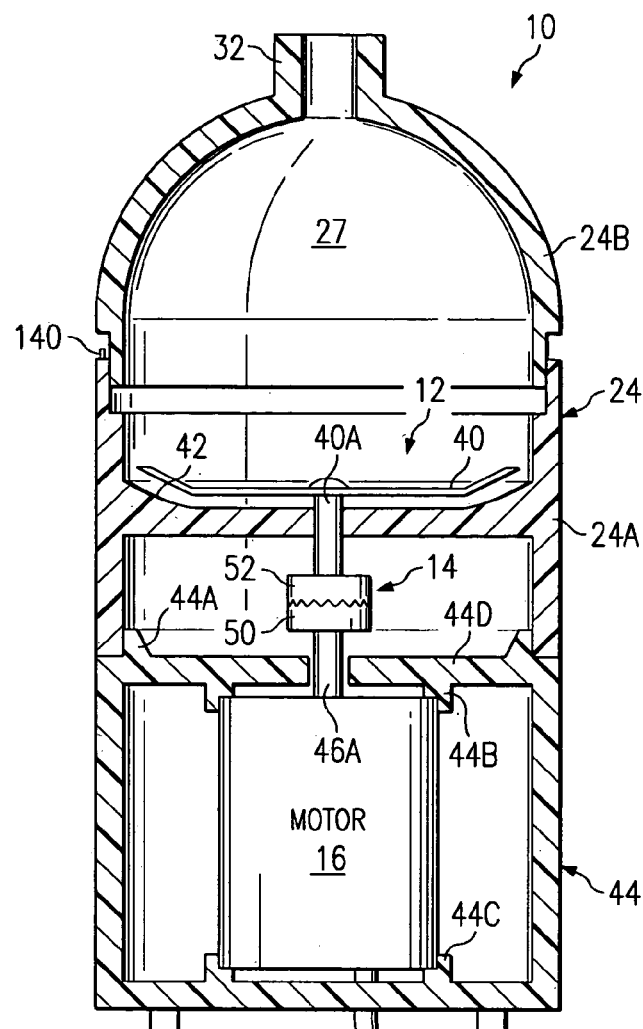
FIG. 14 is a sectional view of an alternate embodiment of the bone mill of the present invention.

In operation, when a user grips the handle body 132 and presses the handle body in the direction E. This activates the switch 134 and further moves the strait shaft 110 and particle reducer 12 in the direction E. When activated, the motor 16 rotates the particle reducer 12 through the coupling 14 (the straight shaft 110 in the present embodiment), thereby causing the blade 40 to pulverize the material 30 in the container 128. It is noted that the container 128 of FIG. 14 is shaped differently than the container of FIG. 13 due, in part, to the different illustrated embodiments of the particle reducer 12.

Figure 18:
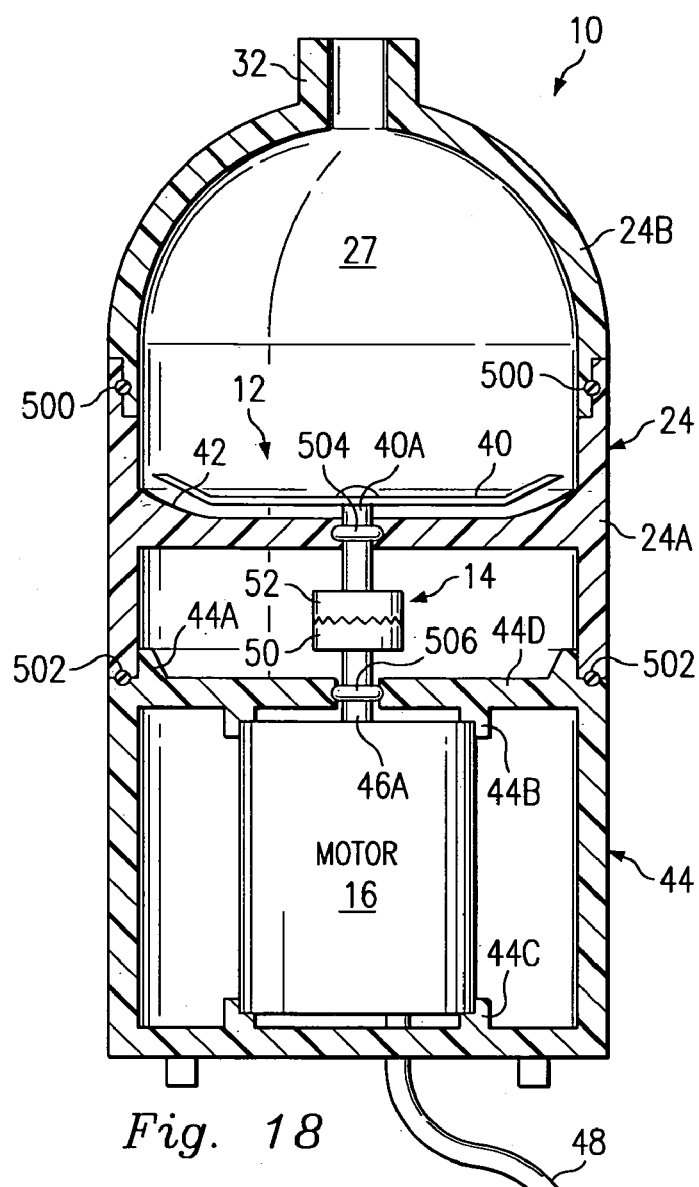
FIG. 18 is a sectional view of an alternate embodiment of the bone mill of the present invention.

Obviously, numerous modifications and variations of the present invention are possible in light of the above teachings. For example, in still yet another embodiment, the bone mill 10 can be altered to include a plurality of sealing arrangements at the various component interfaces. For example, referring to FIG. 18, the bone mill 10 may include an annular sealing arrangement 500 at the interface between the compartment casing body 24A and the cover 24B. In one embodiment, the sealing arrangement 500 is configured as an O-ring that seals between the compartment casing body 24A and the cover 24B. In a similar manner, an annular sealing arrangement 502 may be disposed at the interface between the motor casing 44 and the compartment casing body 24A. The sealing arrangement 502 can also take the form of an O-ring. Moreover, an O-ring seal 504 may be provided at the interface between the compartment casing body 24A and the rotary shaft 40A to prevent the passage of material 30 therethrough. Similarly, an O-ring seal 506 may be provided at the interface between the upper wall 44D of the motor casing 44 and the rotor shaft 46A of the motor 16. Accordingly, the above-described sealing arrangements provide further protection against the escapement of material 32 from the bone mill 10.

Figure 19:
FIG. 19 is a block diagram of circuitry associated with various embodiments of the bone mill of the present invention.

Still further, in other embodiments of the bone mill 10, multi-position switches may be provided to allow a user to select a variety of operating modes for the particle reducer 12. With reference to FIGS. 10 and 19, the switch 90 generally communicates with the motor 16 via a motor control circuit. As can be appreciated, various positions of the switch 90 can correspond to a variety of operating modes of the particle reducer 12, such as, for example, oscillating motion, forward motion, reverse motion, and variable speed control. Accordingly, the bone mill 10 can be adjusted for a variety of operating conditions.

It is understood that certain aspects of one embodiment described above can be combined with aspects of another embodiment to create even more embodiments, as will be readily seen by someone of ordinary skill in the art. It is therefore to be understood that within the scope of the appended claims, the invention maybe practiced otherwise than as specifically described herein.

What is claimed is:

1. An automatic surgical mill for pulverizing bone, comprising:
    a first casing member, the first casing member having an opening for receiving bone into the first casing member;
    a pulverizing bone cutter rotatably supported within the first casing member;
    a second casing member selectively connectable with the first casing member;
    a coupling disposed in the second casing member;
    a first sealing arrangement disposed between the first and second casing members;
    a third casing member selectively connectable with the second casing member;
    a motor drivingly coupled to the pulverizing bone cutter via the coupling; and
    a second sealing arrangement disposed between the second and third casing members;
    wherein the pulverizing bone cutter is configured and operative to pulverize bone received into the first casing member in a manner making the pulverized bone suitable for use in a surgical procedure.

2. The mill of claim 1 wherein the first sealing arrangement is an O-ring.

3. The mill of claim 1 wherein the second sealing arrangement is an O-ring.

4. The mill of claim 1 wherein the cutter includes a blade and a shaft extending from the blade, the shaft being adapted to extend through an opening defined in a wall of the second casing member to engage with the coupling.

5. The mill of claim 4 wherein the motor includes a shaft, the motor shaft being adapted to extend through an opening defined in a wall of the third casing member to engage with the coupling.

6. The mill of claim 5 further comprising a third sealing arrangement, the third sealing arrangement being disposed between the cutter shaft and the wall of the second casing member.

7. The mill of claim 6 further comprising a fourth sealing arrangement, the fourth sealing arrangement being disposed between the motor shaft and the wall of the third casing member.

8. The mill of claim 6 wherein the third sealing arrangement is an O-ring.

9. The mill of claim 7 wherein the fourth sealing arrangement is an O-ring.

10. The mill of claim 1, wherein the pulverizing bone cutter includes a relatively dull blade structure operative to pulverize the bone substantially by impact.

11. The mill of claim 1, wherein the pulverizing bone cutter includes a plurality of blade structures.

12. The mill of claim 11, wherein one of the blades is relatively dull.

13. The mill of claim 12, wherein one of the blades is relatively sharp.

14. The mill of claim 1, wherein the opening extends from an interior of the first casing member to an exterior.

15. An automatic surgical mill, comprising:
    a first casing member, the first casing member having an opening for receiving bone into the first casing member;
    a pulverizing bone cutter rotatably supported within the first casing member;
    a second casing member selectively connectable with the first casing member;
    a coupling disposed in the second casing member;
    a first sealing arrangement disposed between the first and second casing members;
    a third casing member selectively connectable with the second casing member;
    a motor drivingly coupled to the pulverizing bone cutter via the coupling;
    a second sealing arrangement disposed between the second and third casing members; and
    a third sealing arrangement disposed between the bone cutter and the second casing member;
    wherein an interior of the first casing member is substantially devoid of any operational structure other than the pulverizing bone cutter.

16. The surgical mill of claim 15, further comprising a fourth sealing arrangement disposed between the motor and the third casing member.

17. The surgical mill of claim 16, wherein the first, second, third, and fourth sealing arrangement are O-rings.

18. The surgical mill of claim 15, wherein the opening in the first casing member is connectable to a receptacle to receive the pulverized bone and other material for later use.

19. The surgical mill of claim 15, wherein the first casing member is configured and operable to be connected to a syringe.

20. The surgical mill of claim 15, wherein the opening extends from an interior of the first casing member to an exterior.

* * * * *